US006916312B2

(12) United States Patent
Kondo et al.

(10) Patent No.: US 6,916,312 B2
(45) Date of Patent: Jul. 12, 2005

(54) APPLICATOR FOR EXCRETA MANAGEMENT DEVICE

(75) Inventors: Masahiro Kondo, Kobe Hyogo (JP); Roque Yutangco Bautista, Kobe Hyogo (JP); Seika Watanabe, Kobe Hyogo (JP)

(73) Assignee: The Procter & Gamble Company, Cincinnati, OH (US)

( * ) Notice: Subject to any disclaimer, the term of this patent is extended or adjusted under 35 U.S.C. 154(b) by 422 days.

(21) Appl. No.: 10/223,267

(22) Filed: Aug. 19, 2002

(65) Prior Publication Data

US 2003/0045843 A1 Mar. 6, 2003

Related U.S. Application Data

(60) Provisional application No. 60/316,779, filed on Aug. 31, 2001.

(51) Int. Cl.[7] .............................. A61F 5/44; A61F 13/20; A61M 1/00
(52) U.S. Cl. .................. 604/332; 604/277; 604/385.19; 604/393; 604/540
(58) Field of Search ........................... 604/1, 277, 540, 604/317, 327, 332, 355, 385.19, 393, 336–339, 341, 342, 394, 290; 600/362; 15/104.94, 143.1

(56) References Cited

U.S. PATENT DOCUMENTS

| D222,887 S | * | 1/1972 | Weyll, Jr. | ................. D19/34.1 |
| 4,187,850 A | * | 2/1980 | Gust | ........................... 604/338 |
| 4,205,678 A | * | 6/1980 | Adair | ......................... 604/343 |

(Continued)

FOREIGN PATENT DOCUMENTS

| EP | 1 018 324 A1 | 7/2000 | |
| EP | 1 197 194 A1 | * 4/2002 | .......... A61F/5/443 |
| JP | 08-117261 | 5/1996 | |
| WO | WO 95/28139 A1 | 10/1995 | |
| WO | WO 00/00126 A1 | 1/2000 | |
| WO | WO 00/61040 A1 | 10/2000 | |
| WO | WO 01/97722 A1 | 12/2001 | |

*Primary Examiner*—Larry I. Schwartz
*Assistant Examiner*—Michael G. Bogart
(74) *Attorney, Agent, or Firm*—Kevin C. Johnson; Roddy M. Bullock

(57) ABSTRACT

The applicator is used for a placement of an excreta management device on a wearer. The applicator has a longitudinal centerline, a transverse centerline, a device facing surface and an opposing surface. The applicator comprises a handle disposed at transverse ends, a pressure portion disposed along the longitudinal centerline, a middle portion disposed between the handle and the pressure portion and a spacer. When the applicator folded into a pair of right and left pieces along the longitudinal centerline, the spacer is inserted between the right and left pieces. The pressure portion presses the excreta management device toward the wearer's skin during the use of the applicator. The opposing surface of the right piece and the opposing surface of the left piece are separated from one another at the middle portion by the spacer when the applicator is folded. Each of the right and left pieces is deformed such that the distance between the opposing surface of the right piece and the opposing surface of the left piece increases.

8 Claims, 8 Drawing Sheets

U.S. PATENT DOCUMENTS

| | | | | |
|---|---|---|---|---|
| 4,344,433 A | * | 8/1982 | Smith | 604/344 |
| 4,445,898 A | * | 5/1984 | Jensen | 604/337 |
| 4,517,972 A | * | 5/1985 | Finch, Jr. | 602/2 |
| 4,701,168 A | * | 10/1987 | Gammons | 604/310 |
| 4,726,354 A | * | 2/1988 | Fujita | 600/32 |
| 5,312,384 A | | 5/1994 | Temple | |
| 5,473,789 A | * | 12/1995 | Oster | 15/104.94 |
| 5,474,179 A | | 12/1995 | Iosif et al. | |
| 5,562,642 A | * | 10/1996 | Smith et al. | 604/289 |
| 5,753,246 A | | 5/1998 | Peters | 424/404 |
| 6,027,510 A | * | 2/2000 | Alt | 606/108 |
| 6,225,523 B1 | * | 5/2001 | Masini | 602/58 |
| 6,328,720 B1 | * | 12/2001 | McNally et al. | 604/332 |
| 6,336,920 B1 | * | 1/2002 | Temple | 604/355 |
| 6,409,709 B1 | * | 6/2002 | Recto | 604/339 |
| 6,501,002 B1 | * | 12/2002 | Roe et al. | 604/362 |
| 6,579,271 B1 | * | 6/2003 | Aruffo et al. | 604/355 |
| 6,669,677 B2 | * | 12/2003 | Burns et al. | 604/385.19 |
| 6,685,685 B2 | * | 2/2004 | Sugita et al. | 604/355 |
| 6,733,482 B1 | * | 5/2004 | Coles et al. | 604/355 |
| 2001/0007934 A1 | * | 7/2001 | Smith | 604/346 |
| 2003/0040727 A1 | * | 2/2003 | Boulanger et al. | 604/332 |
| 2004/0087919 A1 | * | 5/2004 | Tanaka et al. | 604/327 |
| 2004/0106908 A1 | * | 6/2004 | Leise et al. | 604/332 |

* cited by examiner

US 6,916,312 B2

APPLICATOR FOR EXCRETA MANAGEMENT DEVICE

This application claims benefit of 60/316,779 filed Aug. 31, 2001.

FIELD OF THE INVENTION

The present invention relates to an applicator for an excreta management device used for babies, children or adults. More particularly, the present invention relates to an applicator for providing secure and accurate placement of an excreta management device in the perianal area or urogenital area of a wearer.

BACKGROUND

Excreta management devices are known as articles that are designed to be worn principally by incontinence sufferers and in particular by bedridden patients. Such excreta management devices are attached to the perianal area or urethral area of wearer and are intended to entrap and immediately contain fecal material, urine and other bodily discharges. A representative excreta management device is disclosed in, e.g. U.S. Pat. No. 3,577,989. It discloses a disposable elimination-trapping bag comprising a relatively long and narrow tube. The bag also comprises an aperture and an attachment means comprising an adhesive layer disposed at one extremity of the tube.

A problem naturally associated with such a device is its attachment to the human body. The approach which is mostly used in the field is to provide the device with an adhesive flange which will stick to the perianal or urethral area. The correct placement of the device to the desired area of the skin of a wearer is a key issue in the excreta management devices comprising an adhesive flange. Total or substantial misplacement of the device will lead to a serious problem, in particular, incomplete collection of feces or urine and leakage. For example, if an aperture of an excreta management device is not correctly positioned on an excretory orifice (e.g. an anal opening or a urethra opening) of a wearer, substantial pressure can occur toward the flange of the device in the defecation process. Such substantial pressure can lead to the detachment of the adhesively secured device.

If the misplacement of the device is recognized before use, the placement of the device is normally corrected, typically by the carer. In such a case, the necessary detachment and reattachment of the device to correct the placement of the device cause an additional stress of the affected areas of the skin of the wearer. Many incontinent wearers tend to have a sensitive skin due to their repeated incontinence, and furthermore, sometimes also suffer from skin irritations. Therefore, proper placement of the device in the first place is highly desirable.

A particularly relevant issue in relation to the placement of an excreta management device provided with an adhesive flange is premature sticking. Typically, a release paper which covers the flange is removed at an early step in the application of an excreta management device. In such a case, contact of the exposed adhesive of the flange with any portion of the skin of the caretaker or the wearer will lead to adhesion of at least a portion of the flange to the contacted portion of the skin. In case of a fecal collection device, premature sticking often occurs with portions of the wearer's skin remote from the anal opening intended to make contact with the flange. In case of a urine management device, premature sticking may occur with the thighs of the wearer. Once premature sticking occurs, it becomes difficult to have access of an excreta management device to a correct portion of the skin of the wearer.

Japanese Patent Laid-Open publication 1996-117261 discloses an applicator to assist the adhesive part of the diaper to be disposed to the perianal area. Such an applicator may be useful in the placement of such an incontinence product. However, the successful use of such an applicator will require training, in particular, if the applicator is not specifically designed for its purpose. A further problem with such an applicator is that a caretaker may have only one hand available for the application of the device, for example, when dealing with a bedridden patient. In such a case, it is difficult for the caretaker to correctly dispose the device to desired portions of the wearer by using the applicator. In addition, premature sticking also tends to occur when the applicator is handled by only one hand. The applicator disclosed in Japanese Patent Laid-Open publication 1996-117261 is folded in two along the fold line of the applicator prior to use of the applicator. While such an applicator presses the adhesive part of the diaper along the fold line of the applicator toward the skin of a wearer, it cannot sufficiently press the rest of the adhesive part which is not adjacent the fold line. This may lead to insufficient attachment of the diaper which causes leakage of excreta when excretion occurs.

Accordingly, there still exists a need for an applicator which presses a relatively wide area of an attachment means, such as adhesive, of an excreta management device toward the skin of a wearer.

SUMMARY

The applicator is used for a placement of an excreta management device on a wearer. The applicator has a longitudinal centerline, a transverse centerline, a device facing surface and an opposing surface. The applicator comprises a handle disposed at transverse ends, a pressure portion disposed along the longitudinal centerline, a middle portion disposed between the handle and the pressure portion and a spacer. When the applicator folded into a pair of right and left pieces along the longitudinal centerline, the spacer is inserted between the right and left pieces. The pressure portion presses the excreta management device toward the wearer's skin during the use of the applicator. The opposing surface of the right piece and the opposing surface of the left piece are separated from one another at the middle portion by the spacer when the applicator is folded. Each of the right and left pieces is deformed such that the distance between the opposing surface of the right piece and the opposing surface of the left piece increases.

BRIEF DESCRIPTION OF THE DRAWINGS

While the Specification concludes with claims which particularly point out and distinctly claim the invention, it is believed the present invention will be better understood from the following description of preferred embodiments taken in conjunction with the accompanying drawings, in which like reference numerals identify identical elements and wherein:

DETAILED DESCRIPTION

All cited references are incorporated herein by reference in their entireties. Citation of any reference is not an admission regarding any determination as to its availability as prior art to the claimed invention.

The definitions of several terms are first provided to assist the reader in understanding the present invention.

The term "comprising" means that other steps and other ingredients which do not affect the end result can be added. This term encompasses the term "consisting of" and "consisting essentially of".

The term "disposable" as used herein, describes devices which generally are not intended to be laundered or otherwise restored or reused (i.e., they are intended to be discarded after a single use and, preferably, to be recycled, composted or otherwise disposed of in an environmentally compatible manner.)

The term "excreta" or "bodily discharges", as used herein, are interchangeable, and includes all discharges released from an excretory orifice of a human body, including fecal materials, urine, menses, and the like. The term "excretory orifice", as used herein, refers to an orifice which excreta pass through to discharge the excreta from the human body when excretion occurs. Such an excretory orifice includes urethra, vaginal orifice, anus, and the like.

Figure 1:
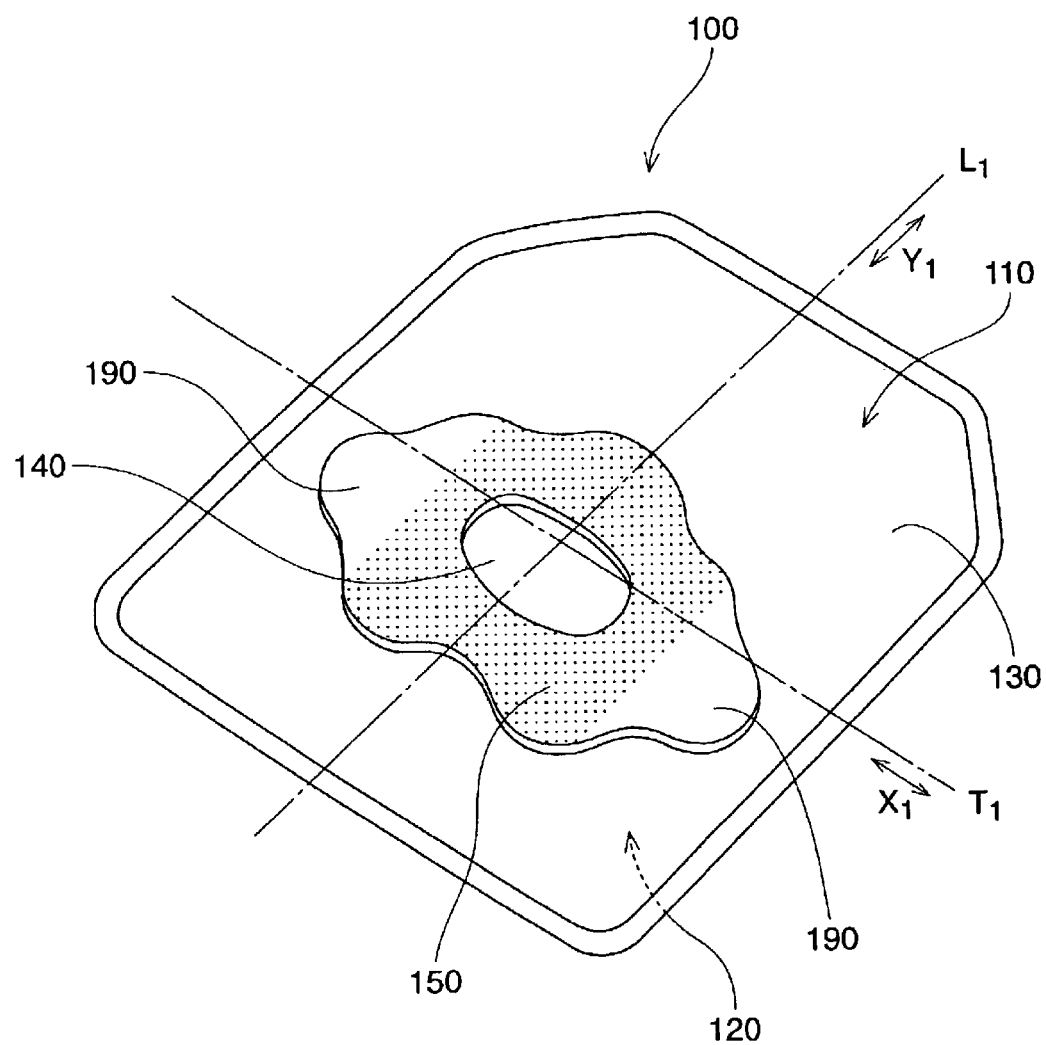
FIG. 1 is a perspective view of one embodiment of an excreta management device used in combination with the applicator of the present invention.
Figure 2:
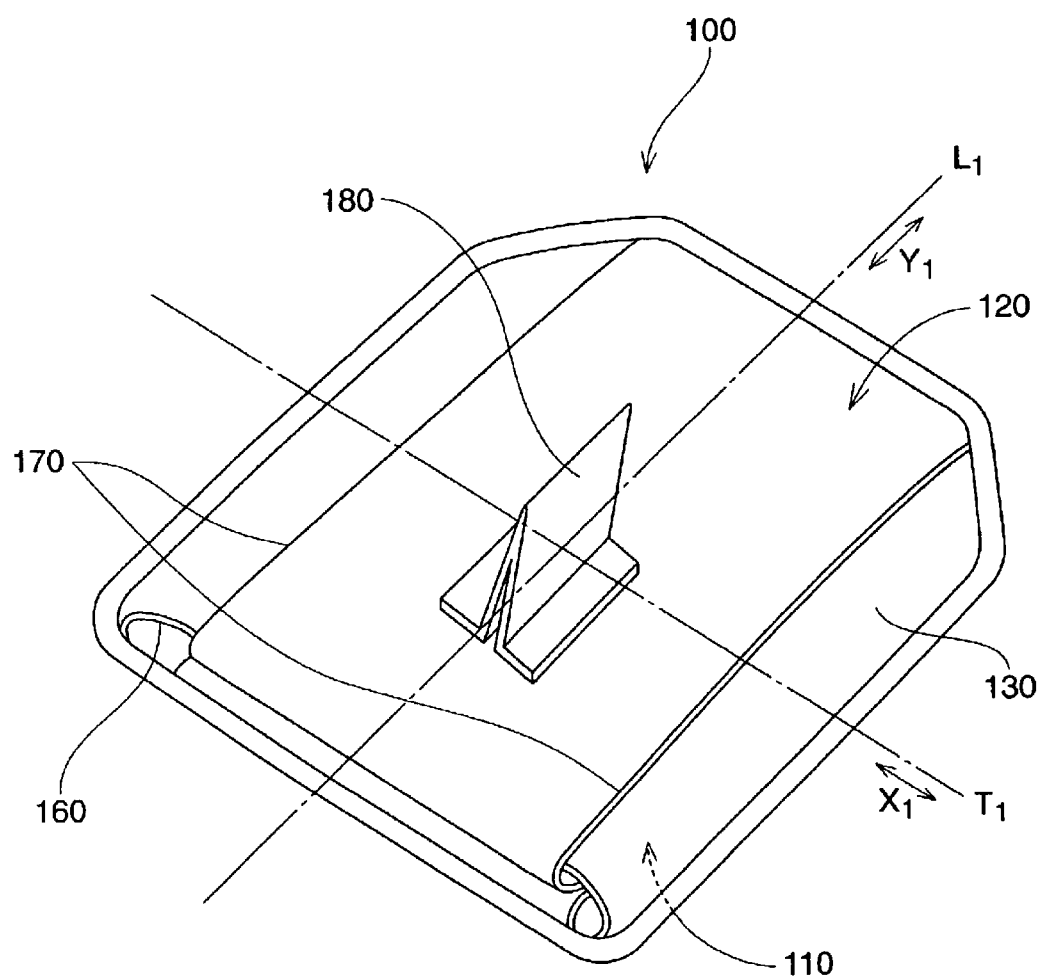
FIG. 2 is a bottom view of the excreta management device of FIG. 1.

FIGS. 1 to 2 show one embodiment of a disposable excreta management device disposed to the area around the excretory orifice (e.g., a perianal area) of a wearer by using an applicator of the present invention. The excreta management device 100 shown in FIGS. 1 and 2 has a longitudinal centerline L1 which runs along the "Y1" axis. The term "longitudinal", as used herein, refers to a line, axis or direction in the plane of the device 100 that is generally aligned with (e.g., approximately parallel to) a vertical plane which bisects a standing wearer into left and right body halves when the disposable excreta management device 100 is worn. The excreta management device 100 shown in FIG. 1 also has a transverse centerline T1. The terms "transverse" or "lateral", as used herein, are interchangeable, and refer to a line, axis or direction which lies within the plane of the disposable excreta management device that is generally perpendicular to the longitudinal direction. The transverse direction is shown in FIGS. 1 and 2 as the "X1" direction. The excreta management device 100 shown in FIGS. 1 to 2 has two surfaces; one is a wearer facing surface 110 and the other is a garment facing surface 120. The wearer facing surface 110 is the surface of the device 100 which is generally oriented toward the wearer when the device 100 is worn. The wearer facing surface 110 typically at least partially comes in contact with the wearer's skin during use of the device 100. The garment facing surface 120 is the surface of the device 100 which is generally oriented away from the wearer when the device 100 is worn, and at least partially toward a garment if a garment is worn. The excreta management device 100 comprises a bag 130 having an opening 140, an adhesive flange 150 surrounding the opening 140 and an assistant tab 180 disposed on the garment facing surface 120 of the bag 130.

The bag 130, as used herein, is a flexible receptacle for the containment of discharged excreta, such as fecal materials, urine or the like. The bag 130 can be provided in any shape or size depending on the intended use thereof, i.e., whether the device is intended for bedridden patients or active patients suffering from incontinence. For example, elongated bags which are principally tubular or rectangular are typically utilized by bedridden patients and elderly incontinence sufferers. For more active wearers such as infants or adults, the excreta management device 100 should preferably be anatomically shaped such that the device 100 follows the contours of the body and can be worn inconspicuously by the wearer under normal garments. Particularly, preferred shapes are three-dimensional shaped bags such as cubic shaped bags, spherical shaped bags, conical (or truncated conical) shaped bags, pyramidal (or truncated pyramidal) shaped bags, tetrahedral (or truncated tetrahedral) shaped bags, cylindrical shaped bags or the like. Further, when the bag is not expanded, the bag may have a substantial circular, oval, square, rectangular, polygonal shape. In a preferred embodiment shown in FIGS. 1 and 2, the bag 130 is a substantial polygonal shape having six sides, which is transversely asymmetric, when the bag 130 is not expanded.

The bag 130 is preferably designed to provide sufficient volume for excreta under a variety of wearing conditions, e.g., when the device 100 is worn by active wearers (i.e., not bedridden wearers). The bag 130 is designed to safely contain any entrapped material, typically it will be liquid impermeable, yet it may be breathable. The bag 130 is designed of sufficient strength to resist rupturing in use, e.g., when pressure on the bag 130 is exerted in typical wearing condition such as sitting.

The bag 130 may be made from a unitary piece of material or from a number of separate pieces of material, which may be identical or different and which are sealed at their respective peripheries, depending on the shape of the bag 130 required.

The bag 130 can comprise one or multiple layers, preferably two or three layers. The layer on the inside of the bag, which will typically at least partially come in contact with excreta, is called the inner layer. The outermost layer of the bag 130, which will typically at least partially come in contact with the skin of the wearer and the garments of the wearer, is called the outer layer. The layer of the bag may be provided from any material such that the bag is liquid impervious. The layer may in particular comprise any material such as a nonwoven or a polymeric film. In a preferred embodiment, the layer may be formed from a laminate comprising a nonwoven layer and a polymeric film. The outer layer of the bag 130 is preferably provided with a nonwoven layer. The nonwoven outer layer presents an compliant surface to the skin of the wearer and thus greatly improves skin healthiness. In one preferred embodiment, the bag 130 comprises two layers, which comprises a nonwoven layer as the outer layer and a film as the inner layer. Alternatively, the bag 130 may comprise three layers; one film layer and two nonwoven layers. Preferably, the film may be interposed between the two nonwoven layers. This sequence of layers results in a closed fibrous structure, which has a particularly pleasing sensation on contact with the skin of the wearer.

Suitable nonwoven layers may comprise felt fabrics, spunlaced fabrics, fluid jet entangled fabrics, air-laid fabrics, wet-laid fabrics, dry-laid fabrics, melt-blown fabrics, staple fiber carding fabrics, spunbonded fabrics, stitch-bonded fabrics, apertured fabrics, combinations of the above or the like. The nonwoven layer or the nonwoven layers constituting the bag 130 may be hydrophobic or hydrophilic. For example, if the bag 130 comprises a film layer, the nonwoven layers may be hydrophilic or hydrophobic. If the bag 130 does not comprise a film layer, preferably at least one nonwoven layer is hydrophobic. It may still be desirable to make both nonwoven layers hydrophobic to ensure that the bag is liquid impervious. Typically, the nonwoven layer is treated with a surface active material, such as a fluorchemical or other hydrophobic finishings, to provide the requisite hydrophobicity. The nonwoven layer, however, may equally be treated with coatings of liquid impervious materials such as hot-melt adhesives or coatings of silicone or other hydrophobic compounds such as rubbers and vegetable and mineral waxes or it may be physically treated using nanoparticulates or plasma coating techniques, for example. The nonwoven layer can also be treated with agents to improve the tactile perceivable softness. The agents include but are not limited to vegetable, animal or synthetic oils, silicone oils and the like. The presence of these agents are known to impart a silky or flannel-like feel to the nonwoven layer without rendering it greasy or oily to the tactile sense of the wearer. Additionally, surfactant material, including anionic, non-anionic, cationic and non-cationic surfactants, may be added to further enhance softness and surface smoothness. Furthermore, the nonwoven layer may be impregnated with a lotion to provide desirable therapeutic or protective coating lotion benefits. The lotion coating is transferable to the skin of the wearer by normal contact and wearer motion and/or body heat. Generally, mineral oil in the form of a lotion is recognized as being effective in imparting a soothing, protective coating to the skin of the wearer. It is also possible to impregnate the nonwoven layer with a solid oil phase of cream formulation or to incorporate into the nonwoven layer an array of pressure- or thermal- or hydrorupturable capsules containing for example, baby oil.

Suitable film materials may comprise a thermoplastic material. The thermoplastic material can be selected from among all types of polyolefins especially polyethylene, polypropylene, amorphous polyolefins, and the like; material containing meltable components comprising fibers or polymeric binders including natural fibers such as cellulose—wood pulp, cotton, jute, hemp; synthetic fibers such as fiberglass, rayon, polyester, polyolefin, acrylic, polyamid, aramid, polytetrafluroethylene metal, polyimide; binders such as bicomponent high melt/low melt polymer, copolymer polyester, polyvinyl chloride, polyvinyl acetate/chloride copolymer, copolymer polyamide, materials comprising blends wherein some of the constituent materials are not meltable; air and vapour permeable materials including microporous films such as those supplied by EXXON Chemical Co., III, US under the designation EXXAIRE or those supplied by Mitsui Chemical Co., Japan under the designation ESPOIR NO; and monolithic breathable materials such as Hytrel™ available from DuPont and Pebax™ available from ELF Atochem, France. In a preferred embodiment, a film which is comprised in any layer is preferably permeable to gases such as air and to vapour such as water vapour in order to avoid the problem of entrapment and condensation of moisture vapour given off by the body of the wearer and thus, the hot, clammy and uncomfortable conditions after a short period of use.

The bag 130 preferably has at least one fold on the garment facing surface 120 in order to expand vertically when the bag 130 contains excreta. The number of the fold will obviously depend upon the circumstances, e.g., a configuration of the bag, a size of the bag and a material of the bag. In the embodiment shown in FIG. 2, folds 160 and 170 are formed on the garment facing surface 120 of the device 100 such that the bag 130 can expand vertically to have a three-dimensional shape when defecation occurs. The expansion of the bag 130 provides extra storage capacity in use. The fold 160 has an alphabet "Z"-like configuration in the cross-sectional view of the garment facing surface 120 of the device 100 taken along the longitudinal direction Y1. Thus, such a fold is referred to as "Z-fold" herein. In the embodiment as shown in FIG. 2, one Z-fold oriented in the transverse direction X1 is formed on the garment facing surface 120 of the device 100. The other folds 170, 170 oriented in the longitudinal direction Y1 are formed on the garment facing surface 120 of the device 100 as shown in FIG. 2. The folds (170, 170) comprise two Z-folds oriented in the longitudinal direction Y1. The two Z-folds (170, 170) are disposed oppositely with respect to the longitudinal centerline L and parallel to the longitudinal centerline L1. The combination of the two opposite Z-folds has a Greek letter "Ω (OMEGA)" like configuration in the cross-sectional view of the garment facing surface 120 of the device 100 taken along the transverse direction X1. Such a combination of two opposite Z-folds is referred to as "OMEGA-fold" herein. Thus, one Z-fold (160) and one OMEGA-fold (170) are formed on the garment facing surface 120 of the device 100 in the embodiment shown in FIG. 2.

The assistant tab 180 is disposed on the garment facing surface 120 of the bag 130 as shown in FIG. 2. The assistant tab 180 is to have the bag 100 expand into a three-dimensional shape easily by pulling the assistant tab 180 after the device 100 is attached to the wearer.

The opening 140 is formed on the wearer facing surface 110 of the device 100 in order to receive excreta such as urine and/or fecal materials from an excretory orifice of the wearer prior to storage within the bag 130 as shown in FIG. 1. The opening 140 is surrounded by the adhesive flange 150 and may be provided in any shape or size, such as circular, oblong, heart shaped and may be symmetrical or asymmetrical, preferably the opening has an oblong configuration either in the longitudinal direction Y1 or in the transversal direction X1.

The adhesive flange 150 is provided at the periphery of the opening 140 in order to attach the device 100 to the skin of a wearer. The adhesive flange 140 may be provided in any size depending on the wearer group for which the device is intended. The adhesive flange 140 may be provided in any shape and preferably has a symmetrical slightly oblong shape in the longitudinal direction Y1 or in the transversal direction X1. The adhesive flange 150 is attached to the wearer facing surface 110 of the device 100 by means known to the person skilled in the art, such as adhesives. The adhesive flange 150 typically comprises an adhesive layer and a substrate to support the adhesive layer.

The substrate of the adhesive flange 150 should be made of soft, flexible and malleable material to allow easy placement of the flange 150 to the skin of a wearer. In addition, the substrate of the adhesive flange 150 may be made of a hydrophobic material and/or a breathable material. Suitable materials for the substrate of the adhesive flange 150 include but are not limited to nonwoven materials, and foams, such as open celled thermoplastic foams. An open-cell foam having a thickness within the general range of about 0.5 to 10 millimeters (preferably about 2 millimeters) has been found particularly effective. Other foam materials or other suitable plastics sheet materials having the described properties of such foams (i.e., softness, pliability, stretchability, contractability, breathability, and hydrophobicity) might be used.

The adhesive layer of the adhesive flange 150 comprises a body-compatible adhesive. The adhesive layer is used in order to fix the device 100 with the skin of a wearer. Preferably, the adhesive layer is covered with a release means to protect the adhesive layer from contamination before use, such as siliconized paper or film. The adhesive layer may cover the entire adhesive flange 150, or alternatively have at least one, preferably a plurality of non-adhesive portions as removal tabs 190 to remove the device 100 from the skin of the wearer easily. The tabs 190 may be adhesive free or may contain inactivated or covered adhesives. The tabs 190 help users remove the device 100 from the skin of a wearer. The adhesive flange 150 is attached to the wearer facing surface 110 of the device 100 by means known to the person skilled in the art, such as adhesives.

Any medically approved water resistant pressure sensitive adhesive may be used for the adhesive layer of the adhesive flange 150 to attach the device to the skin of a wearer, such as hydrocolloid adhesives and hydrogel adhesives. Particularly effective adhesives in providing the desired adhesive properties to secure the adhesive flange 150 to the skin of a wearer around the sensitive excretory orifice area, while allowing for relatively painless application and removal, are hydrophillic hydrogels formed from crosslinking polymers with a plasticizer to form a three-dimensional matrix.

The adhesive can be applied to the substrate of the adhesive flange 150 by any means known in the art such as slot coating, spiral, or bead application or printing. Typically the adhesive is applied at a basis weight of from 20 g/m2 to 2500 g/m2, preferably from 500 g/m2 to 2000 g/m2, more preferably from 700 g/m2 to 1500 g/m2 depending on the end use envisioned. For example for excreta management devices to be used for children the amount of adhesive may be less than for excreta management devices designed for active adult incontinence sufferers.

The applicator 200 is used in combination with the excreta management device 100. The excreta management device 100 is provided with adhesive on the adhesive flange 150 for adhesive attachment to the skin around the excretory orifice of a wearer. For secure attachment of the device 100, pressure needs to be exerted onto the device 100 and the skin of a wearer to ensure adhesion. The applicator 200 allows the user to easily apply sufficient pressure to the device 100 toward the skin of a wearer for adhesive attachment of the device 100. In addition, the applicator 200 allows the user to control such pressure such that pressure is exerted onto the correct/desired area of the skin of a wearer.

Figure 3:
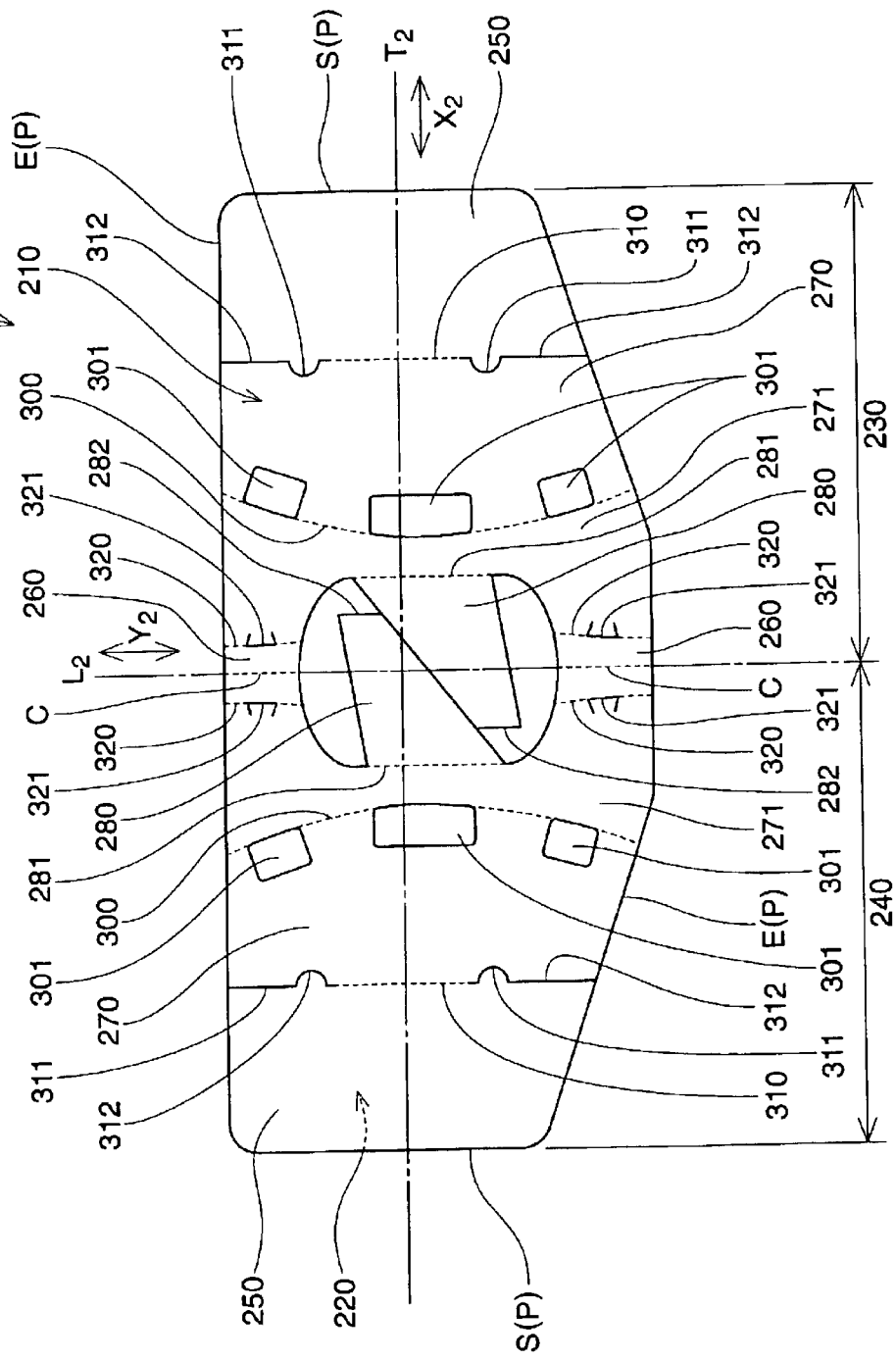
FIG. 3 is a top plan view of one embodiment of an applicator of the present invention.

The applicator 200 is thus used as a supplemental tool for placement of the excreta management device 100 on the skin of a wearer. FIGS. 3 to 6 show a preferred embodiment of such an applicator. The applicator 200 shown in FIG. 3 has a longitudinal centerline L2 which runs along the "Y2" axis and a transverse centerline T2 which is perpendicular to the longitudinal centerline L2 and parallel to the X2 direction. The term "longitudinal", when used for the applicator 200, refers to a line, axis or direction in the plane of the applicator 200 that is substantially parallel to the longitudinal direction L1 of the excreta management device 100 when the applicator 200 is equipped with the device 100. The applicator 200 shown in FIGS. 3 to 6 has two surfaces; one is a device facing surface 210 and the other is an opposing surface 220. The device facing surface 210 is the surface of the applicator 200 which is generally oriented toward the excreta management device 100 when the applicator 200 is equipped with the device 100. The device facing surface 210 typically at least partially comes in contact with the device 100 during use of the applicator 200. The opposing surface 220 is the surface of the applicator 200 which is generally oriented away from the device 100 when the applicator 200 is equipped with the device 100. The applicator 200 has side edges S extending in the direction parallel to the Y2 axis and end edges E extending in the direction parallel to the X2 axis as shown in FIG. 3. The side edges S and the end edges E correspond to the transverse end and the longitudinal end of the applicator 200 respectively. The side edges S and the end edges E define the periphery P of the applicator 200. The applicator 200 is folded into a pair of a right piece 230 and a left piece 240 along the longitudinal centerline L2 when the applicator 200 is equipped with the device 100. Thus, the applicator 200 has a central fold C along the longitudinal centerline L2 as shown in FIG. 3.

The applicator 200 may have any suitable plan view configuration before the applicator 200 is folded into two pieces. Such suitable configurations include, but are not limited to: triangle shape; circle or oval shape; semicircle shape; sector shape; square, rectangular or diamond shape; pentagon shape or any combination of the above. Preferably, the applicator 200 is symmetrical with respect to the longitudinal centerline L2.

The applicator 200 preferably has length and width to allow the excreta management device 100 to be disposed on the skin of a wearer conveniently and accurately. The length of the applicator 200 is measured along the longitudinal centerline L2 in the longitudinal direction. The applicator 200 may have an overall length of between about 60 mm and about 100 mm if the applicator 200 is used for the device 100 designed for adult wearers. In addition, the applicator 200 may have an overall length of between about 45 mm and about 85 mm if the applicator 200 is used for the device 100 designed for infant wearers. The width of the applicator 200 is measured along the transverse centerline T2 in the transverse direction. The applicator 200 may have an overall width of between about 120 mm and about 240 mm if the applicator 200 is used for the device 100 designed for adult wearers. In addition, the applicator 200 may have an overall width of between about 100 mm and about 200 mm if the applicator 200 is used for the device 100 designed for infant wearers.

Construction of the applicator 200 according to the particular size parameters given above results in a product with increased comfort and effectiveness. For example, if the applicator 200 is too smaller than the particular size given above, it is difficult to sufficiently press the excreta management device 100 to the desired area of the skin of a wearer in order to attach the device 100 on the skin of the wearer. Such an insufficient attachment of the device 100 may cause leakage of excreta when excretion occurs. In contrast, if the applicator 200 is too bigger than the particular size given above, it is difficult to make the packaging of the excreta management device 100 in combination with the applicator 200 compact. Such an unnecessary big size of the package of the device 100 in combination with the applicator 200 may cause the costs for transport and packaging product to increase.

The applicator 200 may be made from one unitary piece of material or may comprise several pieces of material. The applicator 200 comprises a spacer 280, preferably, further comprises a handle 250, a pressure portion 260 and a middle portion 270 as shown in FIG. 3. Such elements (i.e., the handle 250, the pressure portion 260, the middle portion 270 and the spacer 280) are joined to each other. The term "joined" or "joining", as used herein, encompasses configurations in which an element is directly secured to another element by affixing the element directly to the other element; configurations in which the element in indirectly secured to the other element by affixing the element to intermediate member(s) which in turn are affixed to the other element; and configurations in which one element is integral with another element, i.e. one element is essentially part of the other element. The handle 250, the pressure portion 260, the middle portion 270 and the spacer 280 may be integral with each other. Alternatively, the handle 250, the pressure portion 260, the middle portion 270 and the spacer 280 may be joined to each other as another element.

Figure 4:
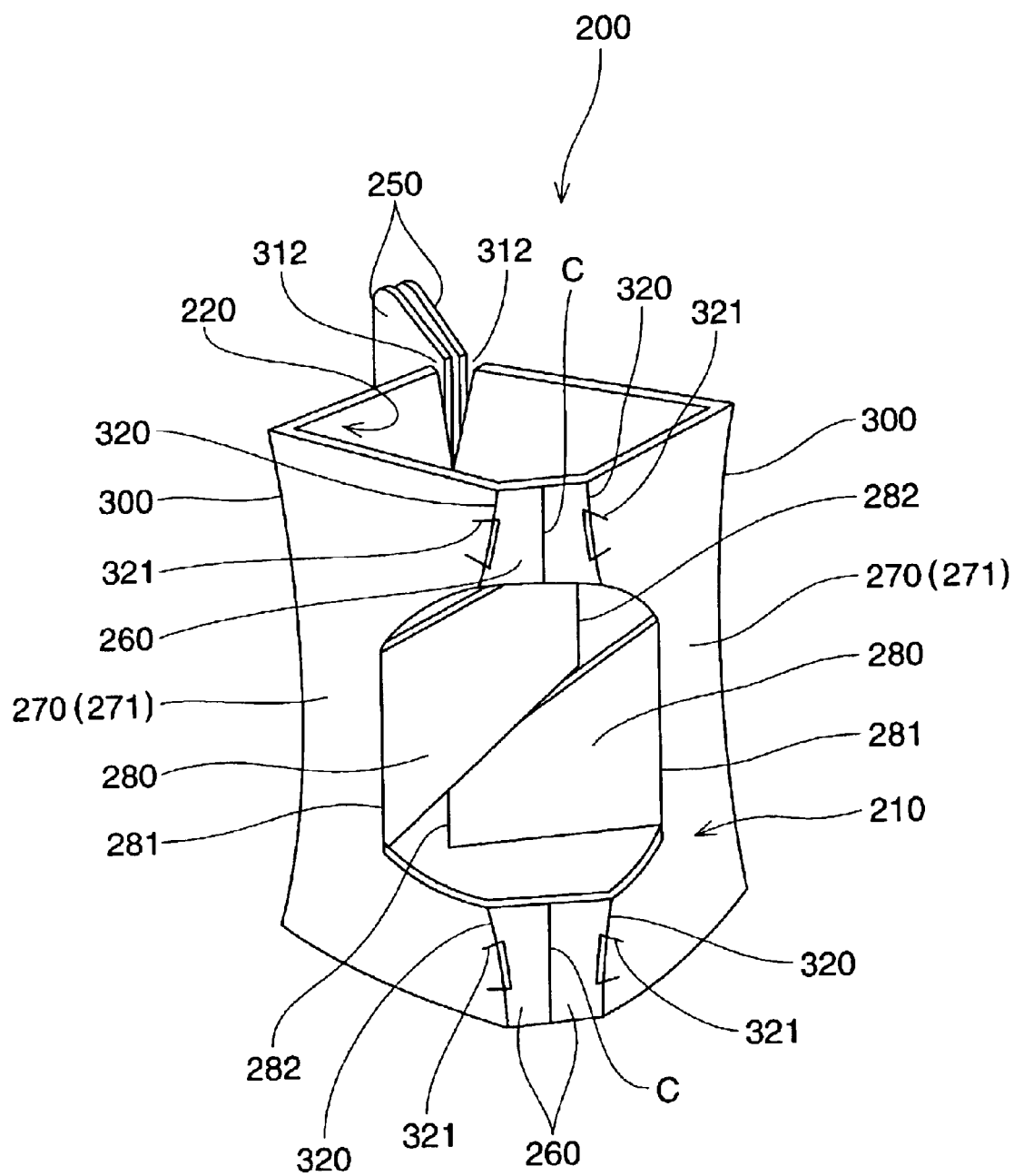
FIG. 4 is a perspective view of the applicator of FIG. 3.
Figure 6:
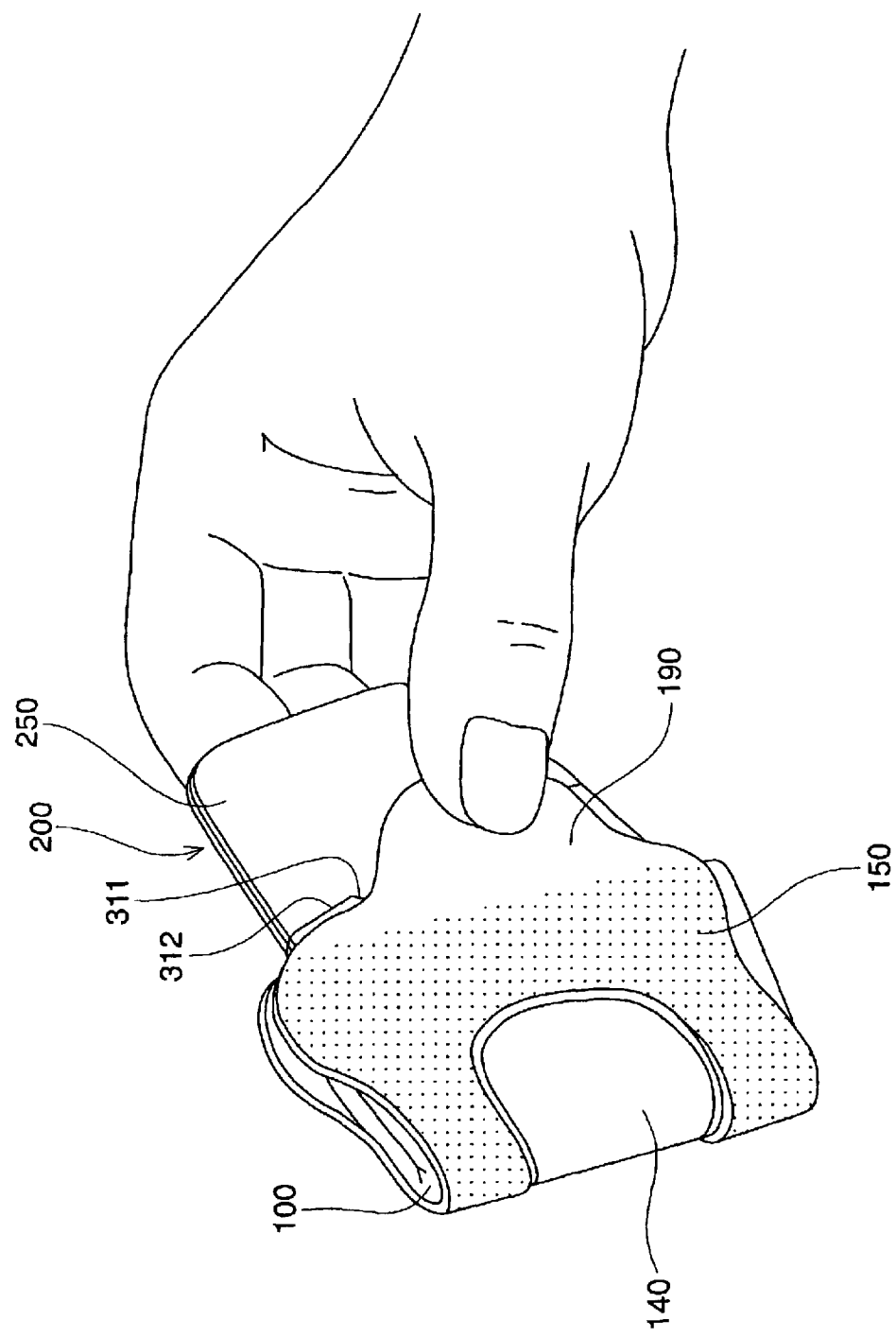
FIG. 6 is a schematic view of the applicator of FIG. 3 in combination with the excreta management device of FIG. 1.

The applicator 200 may further have a first pivot line 300, a second pivot line 310 and a third pivot line 320 in a preferred embodiment. Alternatively, such pivot lines may be omitted from the applicator 200 as long as the applicator 200 is deformed when force to press the device 100 toward the skin of a wearer is applied to the applicator 200. The first pivot line 300 is provided in the middle portion 270, and extending in a direction generally along the longitudinal centerline L2. The second pivot line 310 is provided as a boundary line between the handle 250 and the middle portion 270. The third pivot line 320 is provided as a boundary line between the middle portion 270 and the pressure portion 260. The pivot lines 300, 310 and 320 facilitate the deformation of the applicator 200 when force to press the device 100 toward the skin of a wearer is applied to the applicator 200, and allow the applicator 200 to be deformed into the predetermined shape, e.g., shown in FIG. 4. Any means facilitating the deformation of the applicator 200 upon application of force is with in the scope of the present invention. For example, such means may include any pivotal joint and any flexible means, e.g., a flexible insert such as a rubber insert. Preferably, the pivot lines 300, 310 and 320 may comprise weakened portions 301, 311 and 321 on the pivot lines 300, 310 and 320 as shown in FIG. 3. The pivot lines 300, 310 and 320 comprising such weakened portions further facilitate the deformation of the applicator 200. The examples of the weakened portions may include a fold (i.e., a line of reduced flexure resistance), a pre-pressed portion, an aperture, a line of perforation and/or a slit. Such weakened portions may be continuous or discontinuous. In the embodiment shown in FIG. 3, the first pivot line 300 are a combination of weakened portions comprising a line of folds and discrete apertures, and the second pivot line 310 and the third pivot line 320 are a combination of weakened portions comprising a line of folds and discrete slits. More preferably, a pair of notches 312 may be provided at both longitudinal ends of the second pivot line 310 as shown in FIGS. 3, 4 and 6. When the user grips the handle 250 for holding the applicator 200 folded into two, the right and left pieces 230, 240 of the applicator 200 may bend together in the same direction at the second pivot line 310. This obstructs the deformation of the applicator 200 into the shape shown in FIG. 4 in which the right piece 230 and the left piece 240 at the middle portion 270 separate from one another. The notches 312 prevent the right and left pieces 230, 240 at the middle portion 270 from bending together in the same direction when the handle 250 is gripped by the user. This is because the existence of the notches 312 holds the bend of the right and left pieces 230, 240 at the handle 250 while the handle 250 is gripped by the user. Preferably, the notches 312 may continuously be connected to the weakened portions 311 as shown in FIG. 3. The notches 312 may also work as the above-mentioned weakened portion. In addition, the central fold C formed along the longitudinal centerline L2 may function as a pivot line for the deformation of the applicator 200.

The handle 250 is grasped/held by the user when the applicator 200 is used for placement of the device 100 to the skin of a wearer. The applicator 200 is typically used by a user such as a wearer or a caretaker. The user grasps the handle 250 of the applicator 200 to hold the applicator 200 by one hand. The handle 250 is disposed at the transverse ends of the applicator 200, and may be surrounded by the side edge S, the end edge E and the second pivot line 310. Force to exert pressure to press the device 100 toward the skin of a wearer is initially applied to the applicator 200 through the handle 250 by the user. The handle 250 may comprise one or more pieces joined to the applicator 200, or may be an integral part of the applicator 200.

The pressure portion 260 is formed as an area which contacts the excreta management device 100 during use of the applicator 200. The pressure portion 260 of the applicator 200 exerts pressure toward the adhesive flange 150 of the excreta management device 100 during use of the applicator. The pressure portion 260 is disposed along the longitudinal centerline L2. Preferably, the pressure portion 260 is divided into two portions disposed near both end edges E, E along the longitudinal centerline L2 of the applicator 200 as shown in FIG. 3. More preferably, the pressure portions 260 divided into two portions may be disposed such that they oppose to one another across the spacer 280. The pressure portion 260 may be surrounded by the end edge E and the third pivot line 320. The pressure portions 260 divided into two may have a position and a distance therebetween so as to exert pressure at the skins opposing to one another across the excretory orifice of a wearer, such as an anus. Such a position and/or a distance depend on the intended wearer group (i.e., baby or adult) and on the excreta management device 100 used in combination with the applicator 200. Most insufficient attachment of the adhesive flange 150 of the device 100 tends to occur along the longitudinal centerline L1 of the device 100, and thereby, may lead to the leakage of excreta such as fecal materials or urine out of the device 100. To prevent such insufficient attachment of the device 100 or to improve attachment of the device 100 to the wearer's skin along the longitudinal centerline L1, it is desirable that the adhesive flange 150 is sufficiently pressed toward the skin around the excretory orifice of the wearer along the longitudinal centerline L1. The longitudinal centerline L2 of the applicator 200 corresponds to the longitudinal centerline L1 of the device 100 when the applicator 200 equipped with the device 100. Thus, the pressure portion 260 disposed along the longitudinal centerline L2 is registered with the longitudinal centerline L1 the device 100 when the applicator 200 equipped with the device 100. Such a position of the pressure portion 260 shown in FIG. 3 helps the pressure portion 260 to sufficiently press the device 100 toward the skin around the excretory orifice of a wearer along the longitudinal centerline L1. Preferably, the area of the pressure portion 260 is not so small that damage is done to the excreta management device 100 and/or that pain is caused to the wearer. On the other hand, the area of the pressure portion 260 is preferably not too large regarding the anatomy of an intended wearer such that the applicator 200 exerts pressure only in the area around the excretory orifice of a wearer and/or can be used between the buttocks of a wearer. The pressure portion 260 of the applicator 200 may have a total surface area of between about 300 mm2 and about 600 mm2 if the applicator 200 is used for the device 100 designed for adult wearers. In addition, the pressure portion 260 of the applicator 200 may have a total surface area of between about 200 mm2 and about 600 mm2 if the applicator 200 is used for the device 100 designed for infant wearers. However, the area largely depends on the particular embodiment of the applicator 200 and the excreta management device 100 to be used in combination with the applicator 200. The distance between the pressure portions 260 may be between about 15 mm and about 65 mm if the applicator 200 is used for the device 100 designed for adult wearers. In addition, the distance between the pressure portions 260 may be between about 10 mm and about 65 mm if the applicator 200 is used for the device 100 designed for infant wearers. The pressure portion 260 may comprise one or more pieces joined to the applicator 200, or may be an integral part of the applicator 200.

Figure 5:
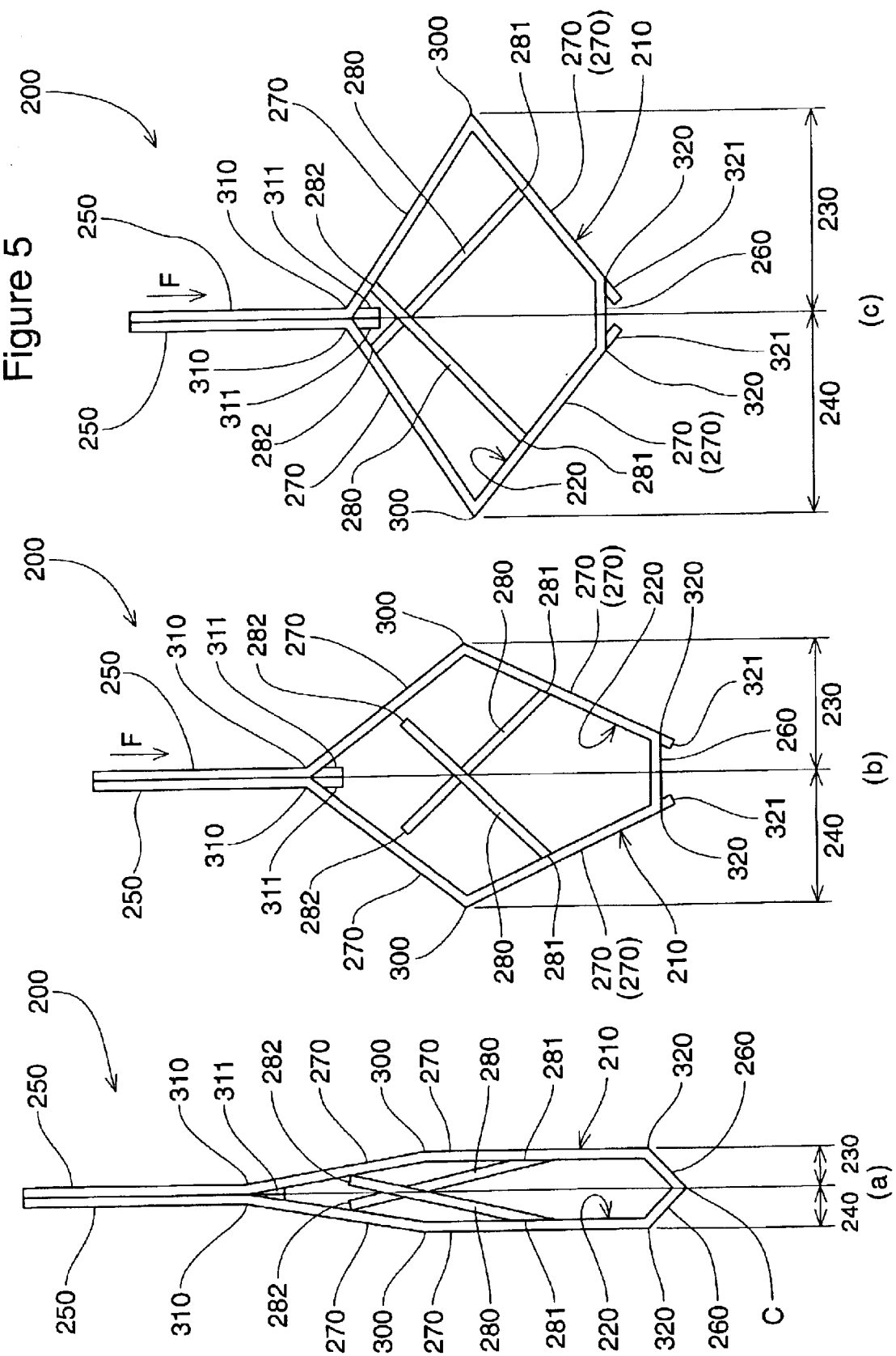
FIG. 5(a) is a first schematic view of the applicator of FIG. 3 before application of force to press the excreta management device toward the skin of the wearer.
FIG. 5(b) is a second schematic view of the applicator of FIG. 3 during application of force to press the excreta management device toward the skin of the wearer.
FIG. 5(c) is a third schematic view of the applicator of FIG. 3 when the applicator is completely deformed by force to press the excreta management device toward the skin of the wearer.

The middle portion 270 is disposed between the handle 250 and the pressure portion 260, and is preferably surrounded by the end edges E, the second pivot line 310 and the third pivot line 320. As shown in FIG. 5, the middle portion 270 is deformed when force to press the device 100 onto the skin of a wearer is applied to the applicator 200 through the handle 250 by the user such that the opposing surface 220 of the right piece 230 and the opposing surface 220 of the left piece 240 are separated from one another at least at the middle portion 270. In a preferred embodiment, the first pivot line 300 may be provided at the middle portion 270, and the middle portion 270 may bend around the first pivot line 300. In addition, the middle portion 270 may have more than two pivot lines. Such deformation of the middle portion 270 forms a contact area 271 which contacts the excreta management device 100 during use of the applicator 200. The contact area 271 presses the adhesive flange 150 of the device 100 toward the skin of a wearer in addition to the pressure portion 260. In particular, the contact area 271 presses portions of the adhesive flange 150 which the pressure portion 260 does not press. Therefore, the applicator 200 can press the wide area of the adhesive flange 150 toward the skin of a wearer for adhesive attachment of the device 100. The area of the middle portion 270 largely depends on the particular embodiment of the applicator 200 and the excreta management device 100 to be used in combination with the applicator 200. In a preferred embodiment, the first pivot line 300 formed at the middle portion 270 may be convexly curved from the transverse ends toward the longitudinal centerline L2. Such a curved contour of the first pivot line 300 enables the contact area 271 of the applicator 200 to uniformly/sufficiently press the device 100 toward the desired area of the skin of a wearer by the user. The middle portion 270 may comprise one or more pieces joined to the applicator 200, or may be an integral part of the applicator 200.

The spacer 280 is formed in order to readily deform the applicator 200 when force to press the device 100 toward the skin of a wearer is applied to the applicator 200 through the handle 250 by the user such that the distance between the opposing surface 220 of the right piece 230 and the opposing surface 220 of the left piece 240 increases. Preferably, the spacer 280 facilitates such deformation of the applicator 200 at the middle portion 270 in order to form the contact area 271. At least a part of the spacer 280 is inserted and disposed between the right piece 230 and the left piece 240 of the applicator 200 when the applicator 200 is folded into a pair of pieces along the longitudinal centerline L2 prior to use. When the applicator 200 is folded into two pieces, the spacer 280 may be partially inserted between the right piece 230 and the left piece 240, or alternatively may be wholly inserted. The existence of the spacer 280 between the right piece 230 and the left piece 240 when the applicator 200 is folded allows easy separation of the opposing surface 220 of the right piece 230 and the opposing surface 220 of the left piece 240 from one another. Such separation between the right piece 230 and the left piece 240 prior to use facilitates the deformation of the applicator 200 during application of force to press that device 100 toward the skin of a wearer and creates the contact area 271 to press the area which the pressure portion 260 does not press. Therefore, the applicator 200 can sufficiently press the wide area of the adhesive flange 150 toward the skin of a wearer for adhesive attachment of the device 100. In a preferred embodiment, the spacer 280 has a fixed end 281 joined to the applicator 200 and a free end 282 opposite to the fixed end 281 as shown in FIGS. 3 to 5. Alternatively, the spacer 280 may not have a free end and the entire spacer 280 may be joined to the applicator 200 as long as the spacer 280 can work to separate the opposing surfaces 220, 220 of the right and left pieces 230, 240 from one another. The fixed end 281 may preferably extend to the applicator 200 in a direction along the longitudinal centerline L2. More preferably, the fixed end 281 may be disposed between the first pivot line 300 and the second pivot line 320. The free end 282 is preferably disposed between the right piece 230 and the left piece 240 when the applicator 200 is folded prior to use. More preferably, the spacer 280 extends in a direction along the transverse centerline T2 such that the free end 282 extends beyond the first pivot line 300 when the applicator 200 is folded. The free end 282 may bias the opposing surface of the middle portion 270 when the applicator 200 is folded such that the distance between the opposing surface 220 of the right piece 230 and the opposing surface 220 of the left piece 240 increases. The spacer 280 may have any suitable configuration. Such suitable configurations include, but are not limited to: triangle shape; circle or oval shape; semicircle shape; sector shape; square, rectangular or diamond shape; flap-like shape; trapezoid shape; pentagon shape or any combination of the above. The applicator 200 may preferably comprise two spacers which have a flap-like shape as shown in FIGS. 3 to 6. However, the number of the spacer 280 is not limited to it and may be practically determined by persons skilled in the art at their discretion depending on the situation. The spacer 280 may comprise one or more pieces joined to the applicator 200, or may be an integral part of the applicator 200.

The process of the deformation of the applicator 200 when force to press the excreta management device 100 toward the skin of a wearer is applied to the applicator 200 is shown in FIGS. 5(*a*), 5(*b*) and 5(*c*). In the embodiment shown in FIGS. 5(*a*), 5(*b*) and 5(*c*), the applicator 200 has the first pivot line 300, the second pivot line 310 and the third pivot line 320, and the spacer 280 has the fixed end 281 joined to the applicator 200 and the free end 282 opposite to the fixed end 281. Before force to press the excreta management device 100 toward the skin of a wearer is applied to the applicator 200, the applicator 200 is folded into two pieces (i.e., the right piece 230 and the left piece 240). After that, when the handle 250 of the applicator 200 is grasped by the user, the opposing surfaces 220 of the right and left pieces 230, 240 of the handle 250 contact with one another as shown in FIG. 5(a). In the embodiment shown in FIG. 5(a), since the spacers 280 are disposed between the right and left pieces 230, 240 at the middle portion 270, the opposing surfaces 220 of the right and left pieces 230, 240 at the middle portion 270 are separated from one another (i.e., there is a space between the right and left pieces 230, 240) even when the handle 250 is grasped by the user. Preferably, the spacer 280 may function as a biasing means to bias the opposing surfaces 220 of the right and left pieces 230, 240 away form one another. Once force F to press the device 100 toward the skin of the wearer is applied to the applicator 200 by the user, the applicator 200 starts to be deformed as shown in FIG. 5(b). Preferably, the deformation of the applicator 200 occurs such that the applicator 200 spreads in a direction perpendicular to the direction of the force F applied from the handle 250 toward the pressure portion 260. The spacer 280 forms space between the right and left pieces 230, 240 before use of the applicator 200. The space formed by the spacer 280 facilitates the deformation of the applicator 200 shown in FIGS. 5(a), 5(b) and 5(c). As shown in FIGS. 5(b) and 5(c), the applicator 200 bends around each of the pivot lines 300, 310, 320. In addition, the deformation of the applicator 200 forms the pressure portion 260 and the contact area 271 as shown in FIGS. 5(b) and 5(c). The pressure portion 260 and the contact area 271 enable the applicator 200 to sufficiently press the wide area of the adhesive flange 150 toward the skin of a wearer for adhesive attachment of the device 100. If force F is further applied to the applicator 200, the free end 282 of the spacer 280 eventually contacts with the opposing surface 220 opposite to the fixed end 281 as shown in FIG. 5(c). This is because the spacer 280 is disposed such that the free end 282 is opposite to the fixed end 281 beyond the first pivot line 300. Once such contact of the free end 282 with the opposing surface 220 occurs, the spacer 280 functions as a stopper to prevent the applicator 200 from being deformed too much. In addition, the contact of the free end 282 with the opposing surface 220 enables the spacer 280 to sufficiently transmit force F to the pressure portion 260. Thus, the user can sufficiently press the excreta management device 100 toward the skin of a wearer for placement of the device 100 on a wearer by using the applicator 200.

The applicator 200 is preferably made of materials which allow the transfer of the required forces from the handle 250 to the pressure portion 260. Preferably, such materials are inexpensive and suitable for a mass manufacturing process. More preferably, the materials are environmentally friendly for disposal, especially, for flushing in a toilet. A suitable material of the applicator 200 may be manufactured from a wide range of materials such as wood, metal, plastic and cardboard. Cardboard may be provided with a coating, e.g., a wax coating to improve the hygienic handling of the applicator 200 and to prevent any dirt from easily sticking to or otherwise soiling the applicator 200. In a preferred embodiment, the cardboard may have a thickness about 0.01 to about 5 mm, preferably, from about 0.1 to about mm, more preferably from about 0.3 to about 0.7 mm. Preferred materials also include those used for tampon applicators which are typically provided from plastics, polymers or flushable smooth surfaced cardboard. Materials such as paper or wood pulp which are used for tampon applicators are also applicable to the applicator 200. The materials disclosed in EP 613672 A1 such as water-soluble polymers having a coating comprising a water-insoluble polymeric material selected from the group consisting of wax (comprising natural wax and synthetic wax), hydrogenated vegetable oil and food grade shellac may also be utilized for the applicator 200.

The applicator 200 may further comprise various labels, e.g., color labels. Such labels can be used to indicate which portion of the applicator 200 is registered with a particular portion of the excreta management device 100. For example, a color label may indicate which portion is to be registered with the center portion of the excreta management device 100. Similarly, color labels on the applicator 200 can be used to indicate how the applicator 200 in combination with the excreta management device 100 is oriented for placement, e.g., with regard to the area around the excretory orifice of the wearer. In addition, the applicator 200 can be labeled to provide usage instructions or any other written instructions.

In a preferred embodiment, the excreta management device 100 is provided in a particular form prior to use of the device 100. In that configuration, the adhesive flange 150 is folded into a pair of two pieces along the longitudinal centerline L1 for the easy placement of the flange 150, e.g., between the buttocks of the wearer. In addition, the bag 130 may be preferably folded such that the bag 130 is completely disposed between the two pieces of the folded adhesive flange 150. More preferably, the excreta management device 100 in combination with the applicator 200 is provided in a particular form prior to use as shown in FIG. 6. Such a form of the device 100 and the applicator 200 provides numerous advantages. For example, folding of the device 100 and the applicator 200 facilitates a compact packaging form of the device 100 and the applicator 200. Thus, it is possible to reduce the costs for transport and packaging material. In addition, the folded device 100 in combination with the applicator 200 enables the user to easily handle the device 100 and the applicator 200 since the device 100 may otherwise cover parts of the applicator 200, e.g., the handle 250. The unfolded device 100 may also cover parts of the skin of the wearer such that the user placing the device 100 cannot sufficiently visually control placement of the device 100.

The applicator 200 may be provided with a means to hold the applicator 200 and the excreta management device 100 together. Such a means will typically also ensure the correct positioning of the applicator 200 relative to the device 100 and/or help to maintain the folded configuration of the device 100 if the device 100 is folded. Such a means preferably are provided in the form of any string or band which may provided in form of a closed loop such as a rubber band. Such a means may also be provided in form of a clamp or a clip made form any suitable material such as plastic or metal.

Figure 7:
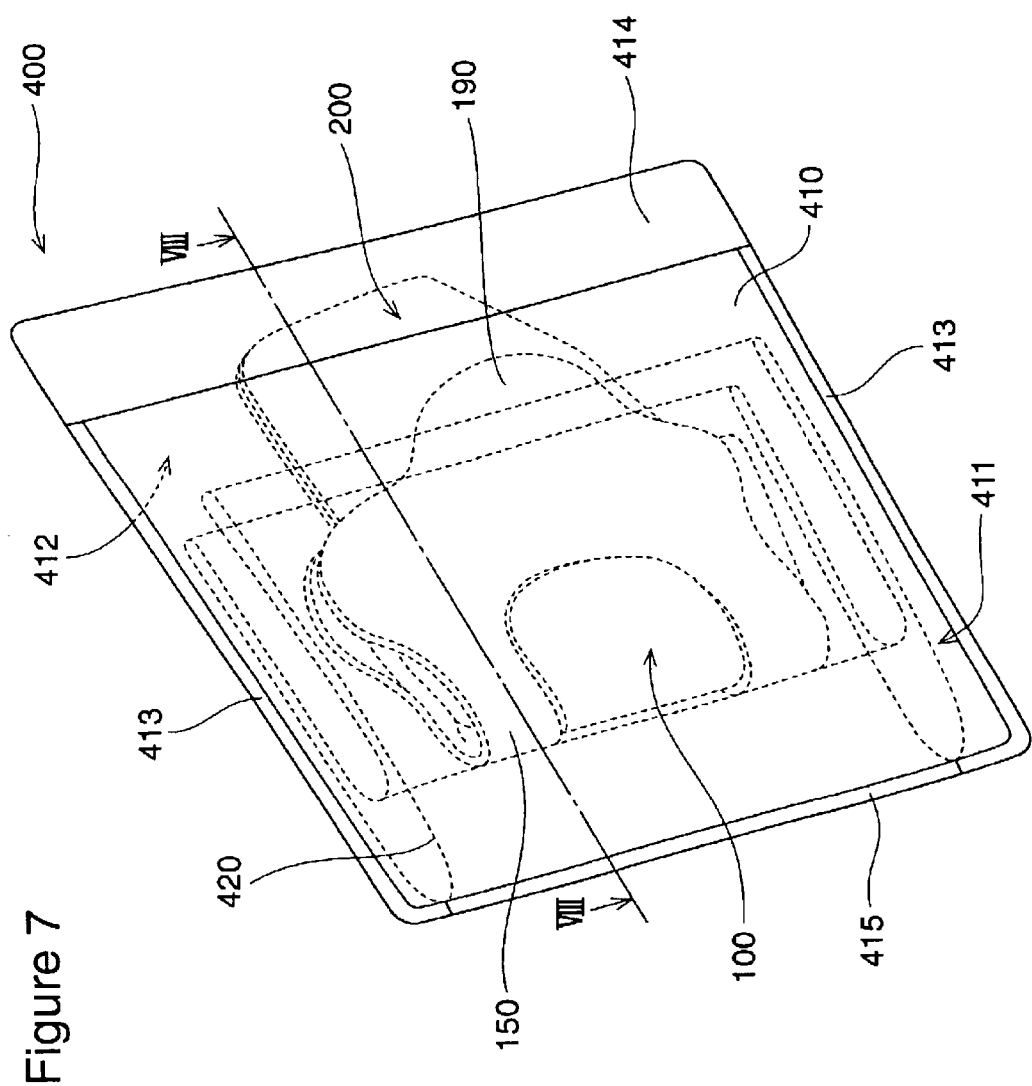
FIG. 7 is a schematic view of the package containing the excreta management device in combination with the applicator.
Figure 8:
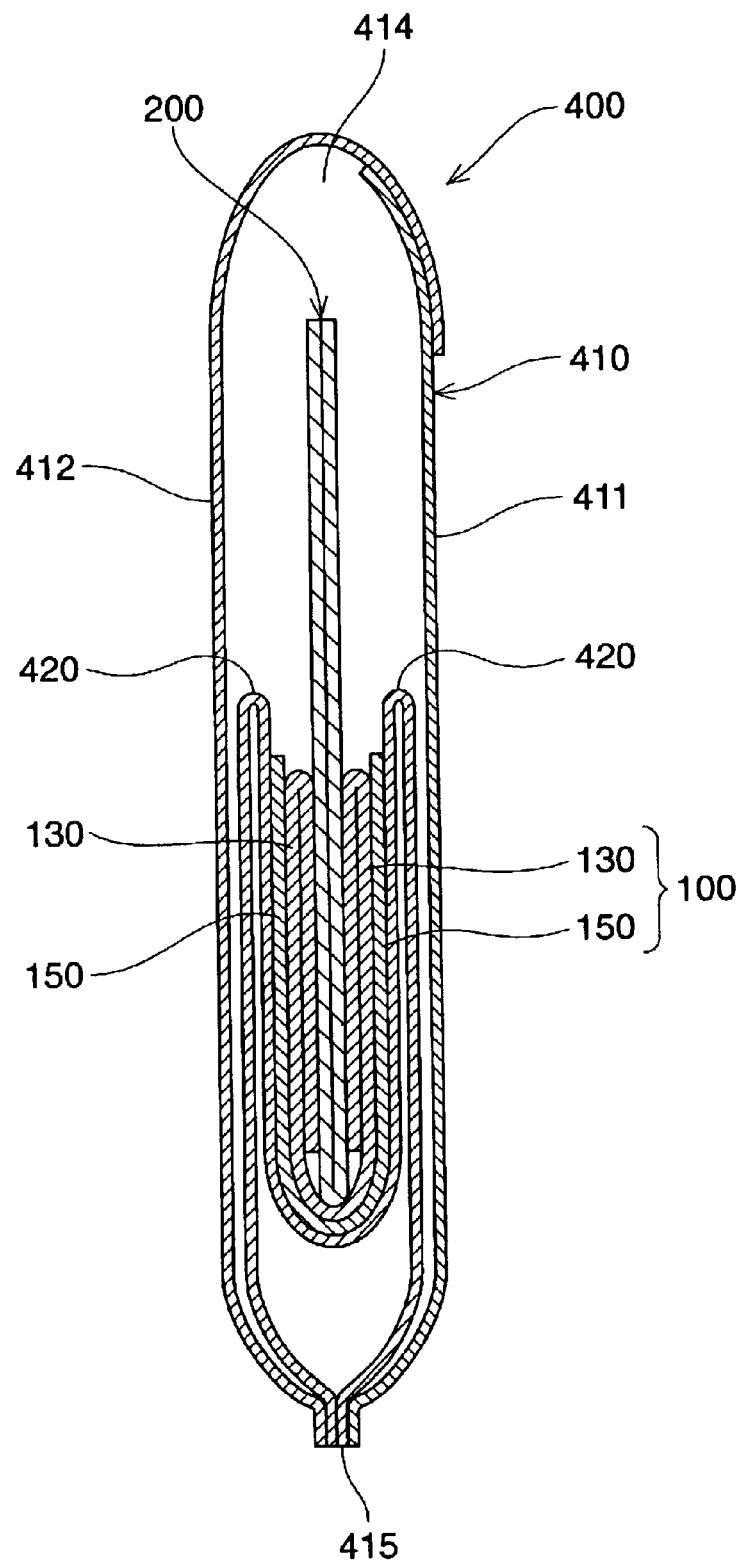
FIG. 8 is a cross-sectional view taken along line VIII—VIII of FIG. 7.

In a preferred embodiment, the excreta management device 100 in combination with the applicator 200 may be packaged as shown in FIGS. 7 and 8. The package 400 shown in FIGS. 7 and 8 comprises an outer cover 410 and an inner release film 420 joined to the outer cover 410. The outer cover 410 comprises a first piece 411 and a second piece 412 sealed along side edges 413 and an end edge 415 by any means known to the person skilled in the art, such as heat seal in order to form a pouched shape. The package 400 has an open edge 414. The first piece 411 and the second piece 412 are temporarily sealed at the open edge 414 by any means known to the person skilled in the art, such as adhesive such that a part of the first piece 411 and a part of the second piece 412 overlap with one another. The user can easily open the outer cover 410 in order to take out device 100 in combination with the applicator 200 therefrom. The inner release film 420 is disposed at the inside of the outer cover 410 in order to completely cover the adhesive constituting the adhesive flange 150 of the device 100. Therefore, the adhesive constituting the adhesive flange 150 can be protected from contamination by the inner release film 420 before use of the device 100. The inner release film 420 is joined to the outer cover 410 at the end edge 415 opposite to the open edge 414 such that the inner release film 420 remains inside of the outer cover 410 when the device 100 is taken out from the package 400 by the user. The user opens the open edge 414 of the outer cover 410 first when the user uses the device 100. The user then grasps the tabs 190 of the device 100 and takes out the device 100 from the package 400. Because the inner release film 420 is joined to the outer cover 410, the adhesive flange 150 of the device 100 is separated from the inner release film 420 after the device 100 is taken out from the package 400, and the adhesive constituting the adhesive flange 150 is exposed for adhesive attachment of the device 100 to the skin of a wearer.

The use of an applicator 200 for placement of the excreta management device 100 according to the present invention preferably comprises the following steps:

(a) Opening the package 400 of the excreta management device 100 in combination with the applicator 200;

(b) Taking out the device 100 and the applicator 200 from the package 400 while gripping both the tabs 190 of the device 100 and the handle 250 of the applicator 200 by using one hand as shown in FIG. 6;

(c) Supporting the body of a wearer, such as wearer's legs by using the other hand for placement of the device 100;

(d) Placing the device 100 in the area around the excretory orifice of the wearer such as the perianal area (or urogenital area) by using the handle 250 of the applicator 200;

(e) Letting the adhesive applied to the adhesive flange 150 of the device 100 attach to the area around the excretory orifice of the wearer by using the applicator 200;

(f) Exerting force to press the device 100 toward the area around the excretory orifice of the wearer through the handle 250 of the applicator 200;

(g) Pressing the entire adhesive provided on the adhesive flange 150 of the device 100 toward the area around the excretory orifice of the wearer through the pressure portion 260 and the contact area 271 of the applicator 200 which are created by the deformation of the applicator 200 shown in FIGS. 5(a), 5(b) and 5(c);

(h) Separating the applicator 200 from the device 100 while holding the handle 250 of the applicator 200;

(i) Unfolding the bag 130 of the device 100;

(j) Pulling the assistant tab 180 disposed on the bag 130 to expand the bag 100 into a three-dimensional shape.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An applicator to be used for placement of an excreta management device on a wearer, the applicator having a longitudinal centerline, a transverse centerline, a device facing surface and an opposing surface, the applicator folded into a pair of right and left pieces along the longitudinal centerline, wherein a spacer is disposed between the right and left pieces to separate the opposing surface of the right piece and the opposing surface of the left piece from one another, and wherein each of the right and left pieces is deformed such that the distance between the opposing surface of the right piece and the opposing surface of the left piece increases.

2. An applicator to be used for placement of an excreta management device on a wearer, the applicator having a longitudinal centerline, a transverse centerline, a device facing surface and an opposing surface, wherein the applicator comprises a handle disposed at transverse ends; a pressure portion disposed along the longitudinal centerline; a middle portion disposed between the handle and the pressure portion; and a spacer, when the applicator is folded into a pair of right and left pieces along the longitudinal centerline, inserted between the right and left pieces, the pressure portion presses the excreta management device toward the wearer's skin during use of the applicator, and the spacer separates the opposing surface of the right piece and the opposing surface of the left piece from one another at the middle portion when the applicator is folded to increase the distance between the opposing surface of the right piece and the opposing surface of the left piece when each of the right and left pieces is deformed.

3. An applicator of claim 2 wherein the spacer has a fixed end joined to the applicator and a free end opposite to the fixed end, the free end disposed between the right and the left pieces when the applicator is folded.

4. An applicator of claim 3 wherein the applicator has a first pivot line provided in the middle portion, the first pivot line extending in a direction along the longitudinal centerline.

5. An applicator of claim 4 wherein the spacer extends in a direction along the transverse centerline such that the free end extends beyond the first pivot line when the applicator is folded.

6. An applicator of claim 4 wherein the first pivot line is convexly curved from the transverse end toward the longitudinal centerline.

7. A disposable excreta management device used in combination with an applicator to be used for placement of the disposable excreta management device on a wearer, the disposable excreta management device comprising a flexible bag to contain excreta and an adhesive flange to attach the device to the skin of a wearer, the flexible bag has an opening surrounded by the adhesive flange, the applicator having a longitudinal centerline, a transverse centerline, a device facing surface and an opposing surface, the applicator folded into a pair of right and left pieces along the longitudinal centerline, wherein a spacer is disposed between the right and left pieces to separate the opposing surface of the right piece and the opposing surface of the left piece from one another.

8. A disposable excreta management device used in combination with an applicator to be used for placement of the disposable excreta management device on a wearer, the disposable excrete management device comprising a flexible bag to contain excreta and an adhesive flange to attach the device to the skin of a wearer, the flexible bag has an opening surrounded by the adhesive flange, the applicator having a longitudinal centerline, a transverse centerline, a device facing surface and an opposing surface, wherein the applicator comprises a handle disposed at transverse ends; a pressure portion disposed along the longitudinal centerline; a middle portion disposed between the handle and the pressure portion; and a spacer, when the applicator is folded into a pair of right and left pieces along the longitudinal centerline, inserted between the right and left pieces, the pressure portion presses the excreta management device toward the wearer's skin during use of the applicator, and the spacer separates the opposing surface of the right piece and the opposing surface of the left piece from one another at the middle portion when the applicator is folded to increase the distance between the opposing surface of the right piece and the opposing surface of the left piece when each of the right and left pieces is deformed.

* * * * *